(12) United States Patent
Singleton

(10) Patent No.: US 11,986,194 B2
(45) Date of Patent: May 21, 2024

(54) TORQUE CABLE

(71) Applicant: Merit Medical Systems, Inc., South Jordan, UT (US)

(72) Inventor: Alex Singleton, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 17/024,297

(22) Filed: Sep. 17, 2020

(65) Prior Publication Data

US 2021/0077133 A1 Mar. 18, 2021

Related U.S. Application Data

(60) Provisional application No. 62/902,134, filed on Sep. 18, 2019.

(51) Int. Cl.
*A61B 17/221* (2006.01)
*A61B 17/00* (2006.01)
*A61B 17/22* (2006.01)

(52) U.S. Cl.
CPC .. *A61B 17/221* (2013.01); *A61B 2017/00424* (2013.01); *A61B 2017/00867* (2013.01); *A61B 2017/22038* (2013.01); *A61B 2017/22079* (2013.01); *A61B 2217/007* (2013.01)

(58) Field of Classification Search
CPC ............ A61M 25/005; A61M 25/0053; A61M 25/0054; A61M 25/09; A61B 17/320032; A61B 2017/320032; A61B 2017/320775; A61B 2017/00424; A61B 2017/007; A61B 2017/00867; A61B 2017/22038; A61B 2017/2279; A61B 5/007; A61B 2090/031; A61B 2090/066

USPC .......................... 606/159, 180; 604/526, 527
See application file for complete search history.

(56) References Cited

U.S. PATENT DOCUMENTS

| | | | |
|---|---|---|---|
| 532,145 A | 1/1895 | Defatsch | |
| 3,049,018 A | 8/1962 | Usskin | |
| 3,416,531 A * | 12/1968 | Edwards | ......... A61M 25/09041 |
| | | | 604/95.04 |
| 4,524,650 A | 6/1985 | Marks | |
| 4,885,003 A | 12/1989 | Hillstead | |
| 5,057,092 A * | 10/1991 | Webster, Jr. | ........ A61M 25/005 |
| | | | 138/123 |

(Continued)

FOREIGN PATENT DOCUMENTS

| | | |
|---|---|---|
| WO | 200117587 | 3/2001 |
| WO | 2018148456 | 8/2018 |

OTHER PUBLICATIONS

Office Action dated Dec. 27, 2021 for U.S. Appl. No. 16/852,105.

(Continued)

*Primary Examiner* — Kankindi Rwego
(74) *Attorney, Agent, or Firm* — Dorsey & Whitney LLP

(57) ABSTRACT

A torque cable that comprises an inner layer and an outer layer. The inner layer includes a plurality of wires that form a braiding pattern. A first set of wires of the inner layer is directed in a proximal direction and a second set of wires of the inner layer is directed in a distal direction. The outer layer includes a plurality of wires that form a braiding pattern. A first set of wires of the outer layer is directed in a proximal direction and a second set of wires of the outer layer is directed in a distal direction.

17 Claims, 8 Drawing Sheets

(56) References Cited

U.S. PATENT DOCUMENTS

| | | | |
|---|---|---|---|
| 5,071,425 A * | 12/1991 | Gifford, III | A61B 17/320783 |
| | | | 264/516 |
| 5,213,015 A | 5/1993 | Disston, Jr. | |
| 5,383,852 A | 1/1995 | Stevens-Wright | |
| 5,702,373 A * | 12/1997 | Samson | A61M 25/005 |
| | | | 604/526 |
| 5,927,345 A * | 7/1999 | Samson | A61M 39/08 |
| | | | 138/123 |
| 6,066,149 A | 5/2000 | Samson et al. | |
| 6,375,615 B1 * | 4/2002 | Flaherty | A61B 17/3417 |
| | | | 600/463 |
| 6,454,779 B1 | 9/2002 | Taylor | |
| 7,037,316 B2 | 5/2006 | McGuckin, Jr. et al. | |
| 7,220,269 B1 | 5/2007 | Ansel et al. | |
| 8,764,779 B2 | 7/2014 | Levine et al. | |
| 8,808,237 B2 | 8/2014 | Thielen et al. | |
| 8,845,621 B2 | 9/2014 | Fojtik | |
| 2001/0031981 A1 | 10/2001 | Evans et al. | |
| 2002/0029052 A1 | 3/2002 | Evans et al. | |
| 2002/0151918 A1 | 10/2002 | Lafontaine et al. | |
| 2002/0169414 A1 | 11/2002 | Kletschka | |
| 2003/0040704 A1 | 2/2003 | Dorros et al. | |
| 2003/0055445 A1 | 3/2003 | Evans et al. | |
| 2005/0268750 A1 | 12/2005 | Bruce et al. | |
| 2007/0208361 A1 | 9/2007 | Okushi et al. | |
| 2008/0033467 A1 | 2/2008 | Miyamoto et al. | |
| 2008/0082107 A1 | 4/2008 | Miller et al. | |
| 2008/0125798 A1 | 5/2008 | Osborne et al. | |
| 2008/0234722 A1 | 9/2008 | Bonnette et al. | |
| 2008/0277445 A1 | 11/2008 | Zergiebel | |
| 2009/0030274 A1 | 1/2009 | Goldfarb et al. | |
| 2010/0023033 A1 | 1/2010 | Mauch et al. | |
| 2010/0249817 A1 | 9/2010 | Mark | |
| 2011/0082490 A1 | 4/2011 | Connelly et al. | |
| 2011/0282279 A1 | 11/2011 | Wayman et al. | |
| 2012/0059356 A1 | 3/2012 | Di Palma et al. | |
| 2012/0239008 A1 | 9/2012 | Fojtik | |
| 2012/0277671 A1 | 11/2012 | Fuentes | |
| 2012/0316586 A1 | 12/2012 | Demarais et al. | |
| 2013/0289578 A1 | 10/2013 | Noriega et al. | |
| 2014/0142594 A1 | 5/2014 | Fojtik | |
| 2014/0228869 A1 | 8/2014 | Bonnette et al. | |
| 2014/0277015 A1 | 9/2014 | Stinis | |
| 2015/0305765 A1 | 10/2015 | Fojtik | |
| 2015/0314074 A1 | 11/2015 | Howlett et al. | |
| 2015/0374483 A1 | 12/2015 | Janardhan et al. | |
| 2016/0015505 A1 | 1/2016 | Johnson et al. | |
| 2016/0038174 A1 | 2/2016 | Bruzzi et al. | |
| 2016/0066933 A1 | 3/2016 | Root et al. | |
| 2016/0270813 A1 | 9/2016 | Chida | |
| 2016/0331468 A1 | 11/2016 | Lee et al. | |
| 2017/0020556 A1 | 1/2017 | Sutton et al. | |
| 2017/0238960 A1 | 8/2017 | Hatta et al. | |
| 2017/0252057 A1 | 9/2017 | Bonnette et al. | |
| 2018/0042628 A1 | 2/2018 | Panian | |
| 2018/0126119 A1 | 5/2018 | Mcniven et al. | |
| 2018/0235652 A1 | 8/2018 | Banjamin et al. | |
| 2018/0242989 A1 | 8/2018 | Nita | |
| 2018/0271556 A1 | 9/2018 | Bruzzi et al. | |
| 2020/0078029 A1 | 3/2020 | Hansen | |
| 2020/0246029 A1 | 8/2020 | Singleton et al. | |

OTHER PUBLICATIONS

International Search Report and Written Opinion dated Mar. 23, 2021 for PCT/US2020/051270.
Office Action dated Apr. 15, 2021 for U.S. Appl. No. 16/563,390.
International Search Report and Written Opinion dated Jan. 3, 2020 for PCT/UA2019/049974.
International Search Report and Written Opinion dated Jan. 6, 2017 for PCT/US2016/053932.
International Search Report and Written Opinion dated Jun. 1, 2020 for PCT/US2020/015721.
Notice of Allowance dated Sep. 11, 2019 for U.S. Appl. No. 15/277,473.
Office Action dated Apr. 22, 2019 for U.S. Appl. No. 15/277,473.
Office Action dated Nov. 29, 2018 for U.S. Appl. No. 15/277,473.
SPINR Product Brochure, Rights acquired by Merit Medical Systems, Inc. ,Jul. 2015.
Office Action dated Aug. 25, 2021 for U.S. Appl. No. 16/563,390.
Office Action dated Aug. 31, 2021 for U.S. Appl. No. 16/776,336.
Office Action dated Sep. 8, 2022 for U.S. Appl. No. 16/776,336.
Oval English Definition and Meaning, 2022.
Office Action dated Mar. 16, 2023 for U.S. Appl. No. 16/776,336.
Office Action dated Sep. 14, 2023 for U.S. Appl. No. 16/776,336.

* cited by examiner

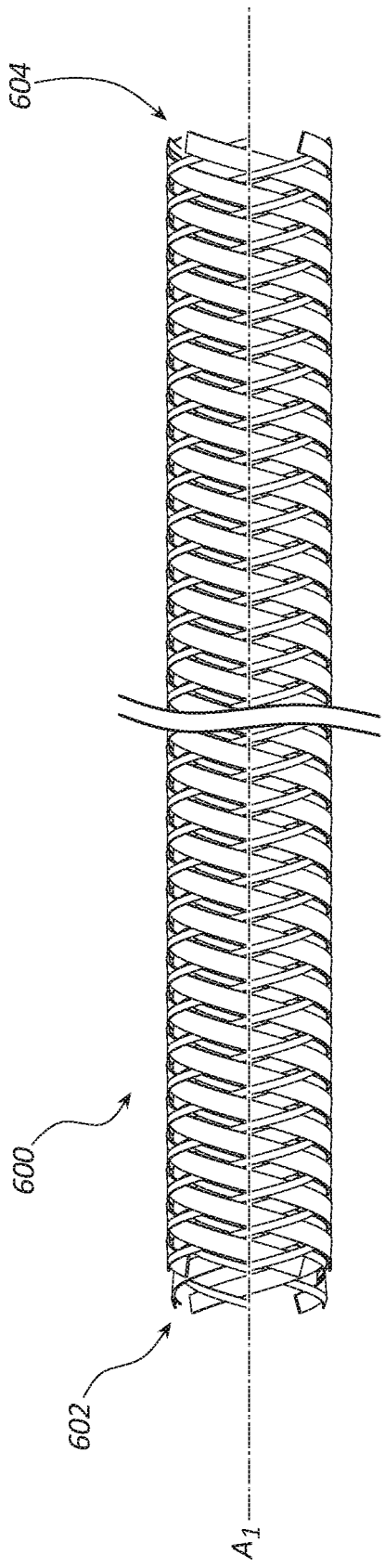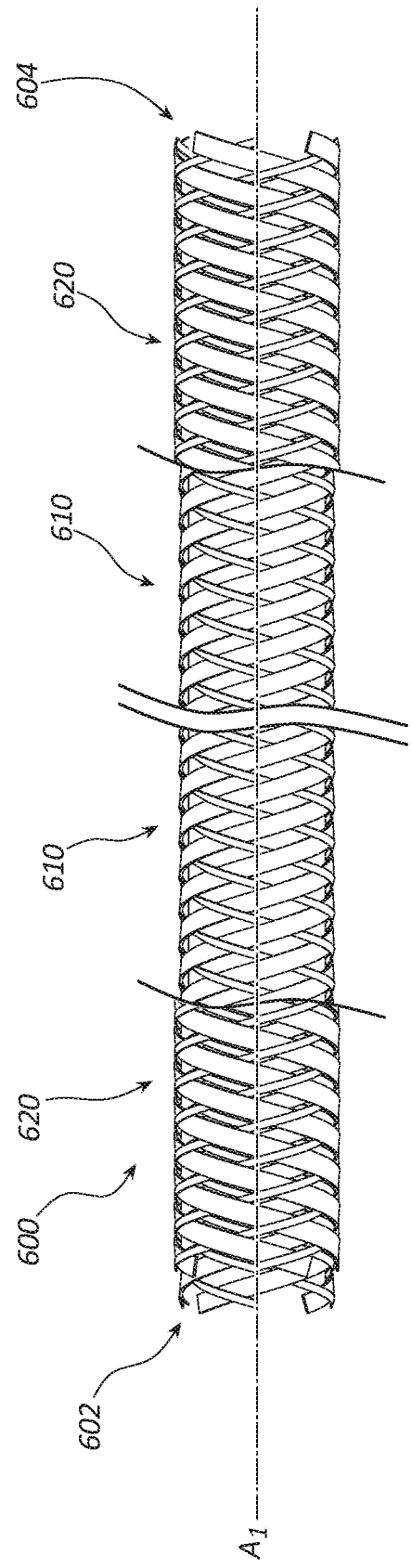
FIG. 4A
FIG. 4B

TORQUE CABLE

RELATED APPLICATIONS

This application claims priority to U.S. Provisional Patent Application No. 62/902,134, filed on Sep. 18, 2019 and titled, "Torque Cable," which is hereby incorporated by reference in its entirety.

TECHNICAL FIELD

The present disclosure relates generally to the field of torque cables. Some embodiments of the present disclosure relate to torque transfer in rotating apparatuses and methods for macerating clots within the vasculature.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 4A is a side view of a torque cable according to one embodiment.

FIG. 4B is a breakaway view of the torque cable of FIG. 4A.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical interaction. Thus, two components may be coupled to each other even though they are not in direct contact with each other. The phrases "attached to" or "attached directly to" refer to interaction between two or more entities that are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 1:
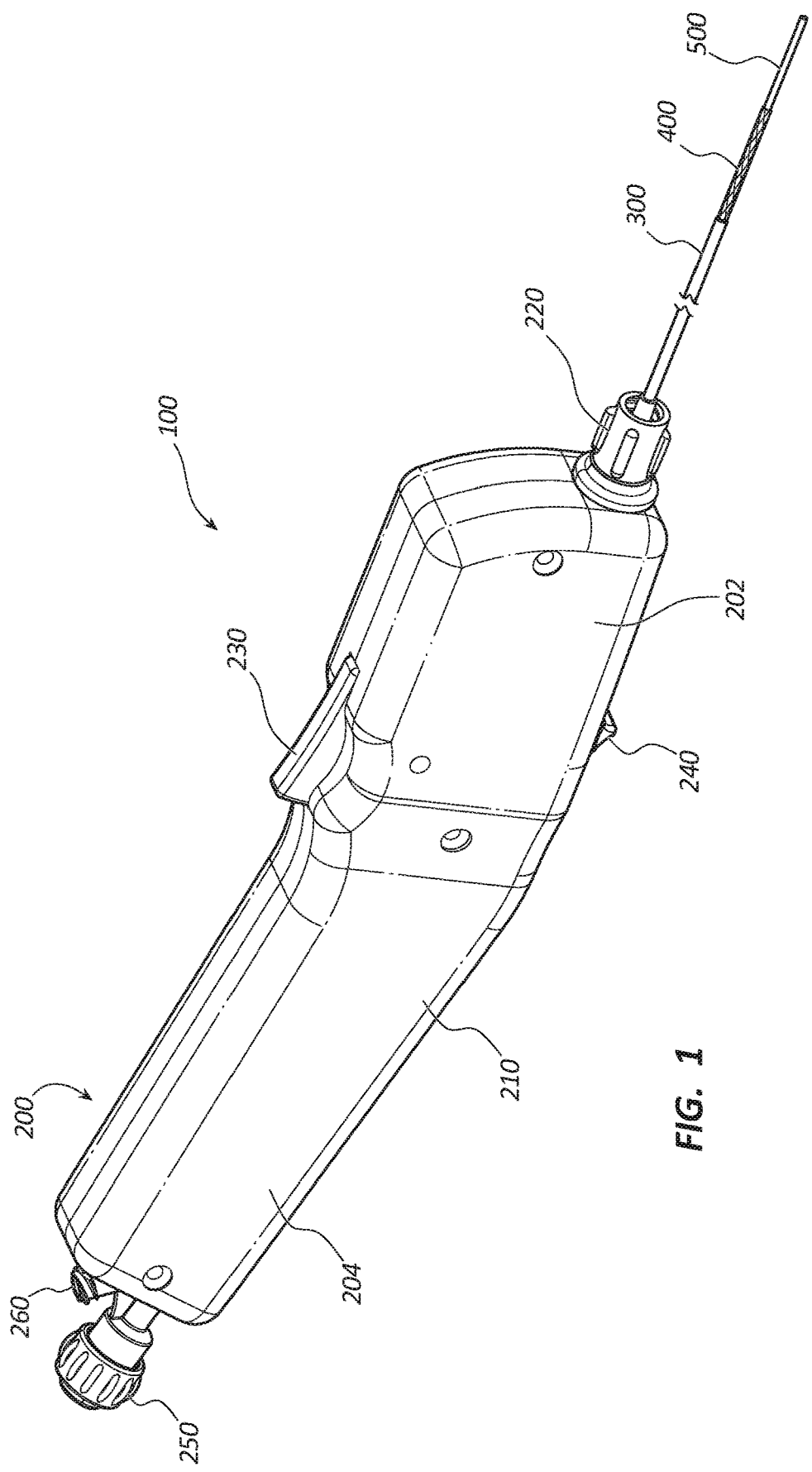
FIG. 1 shows a perspective view of a thrombosis macerating device comprising a handle and a catheter according to one embodiment.

FIG. 1 illustrates a perspective view of a macerating device 100 that comprises a handle 200, a catheter 300, a macerating element 400, and a guidewire 500. The macerating element 400 of the macerating device 100 may be configured to rotate to macerate or displace a clot or blockage, such as in vascular thrombosis. In some embodiments, the macerating device 100 may be configured to macerate a clot or blockage into small components in the venous vasculature. In some such embodiments the macerated small components may be sufficiently small as to reduce or minimize the risk of a pulmonary embolism.

The macerating element 400 may include an expandable basket 410 (see FIG. 3) that is configured to expand and collapse. In a collapsed configuration, the expandable basket 410 may be disposed or partially disposed within the catheter 300 and the catheter 300 may be deployed within the vasculature of a patient to a desired location to treat a blockage or clot. The expandable basket 410 may be expanded to an expanded configuration and rotated to macerate the desired blockage or clot. In some instances, the clot or blockage may be aspirated after being macerated.

The handle 200 may comprise a housing 210 for housing the various components of the macerating device 100. For example, the housing 210 may house a motor for rotating the expandable basket 410. The housing 210 may also house a power source to power the motor.

The handle 200 may further include a coupler 220. In some embodiments, the catheter 300, the macerating element 400, and the guidewire 500 may be coupled to the handle 200 via the coupler 220. Embodiments where these components are removably coupled as well as embodiments wherein these elements are fixedly coupled are within the scope of this disclosure.

The handle 200 may further include a rotational speed control mechanism configured to control the rotational speed of the macerating element 400. The rotational speed control mechanism may be a trigger 230 disposed on a top surface of the handle 200. The trigger 230 may enable a user, such as a medical professional, to control the rotational speed of the macerating element 400, e.g., the expandable basket 410.

The macerating device 100 may be configured to rotate the expandable basket 410 in a clockwise or a counterclockwise direction. In various embodiments, and in various procedures, the expandable basket 410 may rotate at various rotational speeds, including 0-10,000 rpm; 500-10,000 rpm; 500-2,500 rpm; and 1,000-5,000 rpm. Further, systems configured to rotate the expandable basket 410 at rotational speeds of at least 500 rpm; at least 1,000 rpm; at least 500 rpm and up to 10,000 rpm; less than 500 rpm; less than 250 rpm; and less than 200 rpm are also within the scope of this disclosure.

In some embodiments, the trigger 230 may be configured to rotate the expandable basket 410 at any number of predetermined rotational speeds. For example, the trigger 230 may be configured with set points correlating to a high speed, a medium speed, and a low speed. The trigger 230 may be configured, for example, with distinct regions that correlate to such set points. For example, a first region may correspond with a low speed, for example, 500 rpm to 2,500 rpm. A second region may correspond with a medium speed, for example, 1,000 rpm to 5,000 rpm. A third region may correspond with a high speed, for example, 5,000 rpm to 10,000 rpm.

The handle 200 may further include a diameter control mechanism configured to control or change the diameter of the expandable basket 410. The diameter control mechanism may be a slider 240 operatively coupled to the expandable basket 410 such that displacement of the slider 240 variably alters the diameter of the expandable basket 410. In the illustrated embodiment, the slider 240 is configured to be displaced in a direction parallel to a longitudinal axis of the handle 200. In other embodiments, the slider 240 may be configured to be displaced in other directions. During a procedure, the user may manipulate the slider 240 to set, for example, a maximum diameter of the expandable basket 410. For example, during a procedure, the user may manipulate the slider 240 to lock the maximum diameter of the expandable basket 410 at a diameter that is less than the diameter of a target vessel to avoid damaging the vessel during the macerating procedure.

In some embodiments, the slider 240 may include a plurality of detents. The detents may lock the slider 240 in place until a predetermined amount of force is applied to the slider 240 to release it from the detent until it reaches the next detent. Each detent may correspond with a predetermined diameter of the expandable basket 410. In some embodiments, the predetermined diameter may correlate to a maximum diameter of the expandable basket 410. That is, in some embodiments, the expandable basket 410 may be compressible to a smaller diameter (due, for example, to external constraining forcing acting on the outside diameter of the expandable basket 410) though the position of the slider 240 controls the maximum size of expansion of the expandable basket 410.

The handle 200 may be designed to fit ergonomically within the hand of the user, thus the macerating device 100 may be configured as a handheld device. The handle 200 may include a distal portion 202 and a proximal portion 204. The proximal portion 204 may be angled relative to the distal portion 202, facilitating griping of the proximal portion 204 with the palm while positioning the hand to manipulate the trigger 230 and the slider 240 with the thumb and fingers. For example, the user could manipulate the trigger 230 with their thumb and manipulate the slider 240 with their index finger.

The handle 200 may further include a second port 250. The second port 250 may communicate with a lumen disposed within the macerating element 400. The second port 250 may be in communication with the lumen of the handle and in communication with a first port in the coupler 220. Thus, the user may advance an elongate component, such as the guidewire 500, through the second port 250 and the lumen of the handle 200 and through the first port in the coupler 220. The elongate component may then extend into the lumen of the macerating element 400. Furthermore, the second port 250 may be in fluid communication with the lumen of the macerating element 400. In such instances, the second port 250 may function as an aspiration or infusion port for aspiration or infusion of materials, including aspiration of clots or other matter and/or infusion of medication, saline, etc. For example, the user may infuse a medication, such as tPA, to help break up the clot or blockage before the user attempts to macerate the clot or blockage. In some embodiments, a vacuum source may be applied to the second port 250 to aspirate the macerated clot or blockage.

The handle 200 may further include a third port 260. The third port 260 may be in communication with a second lumen, such as a lumen disposed within the catheter 300 between the macerating element 400 and the catheter 300. The third port 260 may also function as an aspiration or infusion port. In some embodiments, a vacuum source may be applied to the third port 260 to remove the macerated clot or blockage. In some embodiments, the user may infuse a medication, such as tPA, to help break up the clot or blockage.

Figure 2:
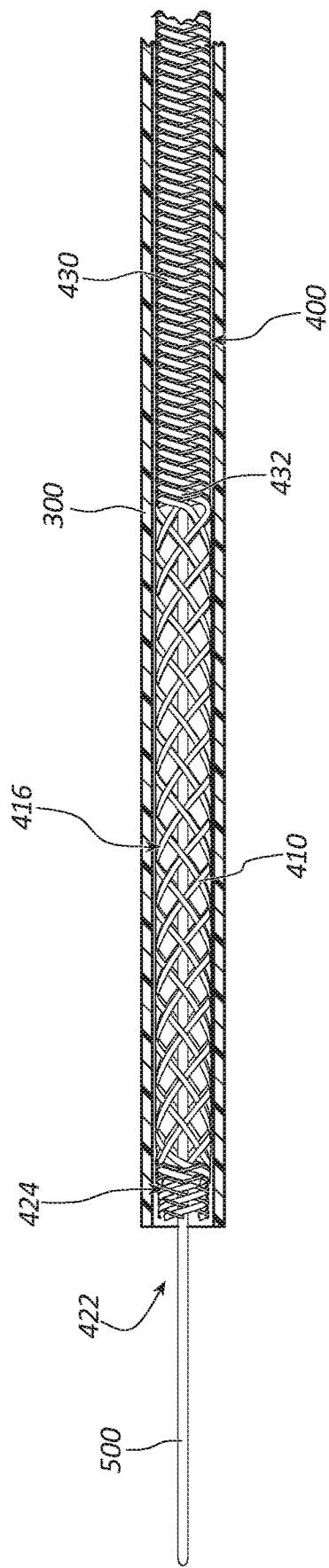
FIG. 2 shows a detailed view of an expandable basket of the macerating device in a collapsed configuration according to one embodiment.
Figure 3:
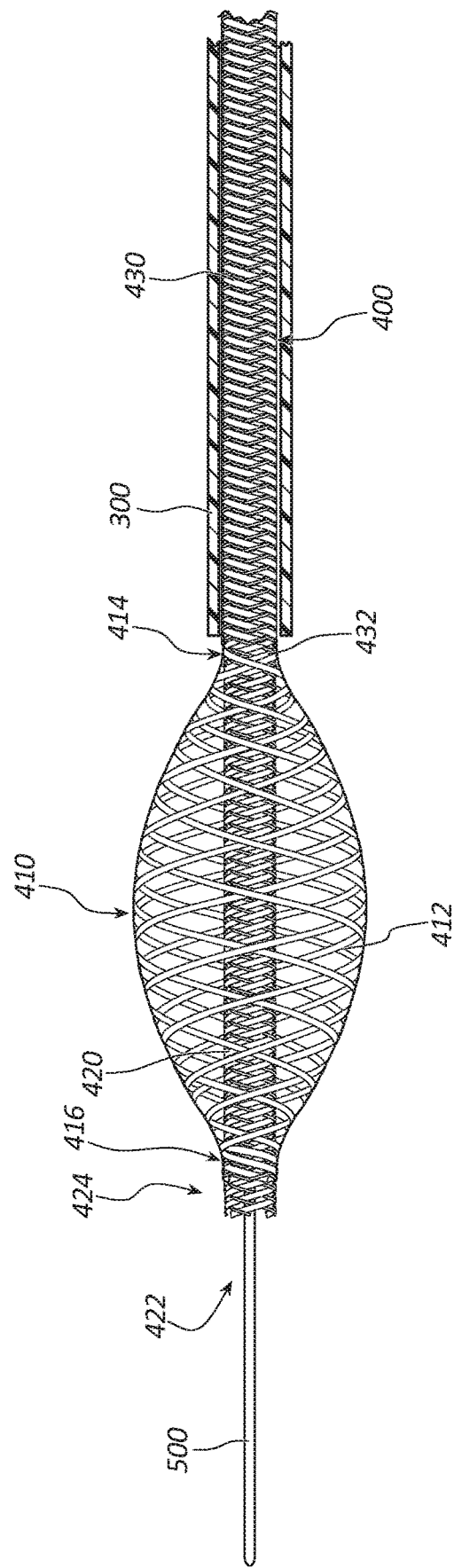
FIG. 3 shows a detailed view of the expandable basket of FIG. 2 in an expanded configuration.

FIGS. 2 and 3 illustrate a detailed view of the distal end of the catheter 300, the macerating element 400, and the guidewire 500. FIG. 2 illustrates the expandable basket 410 disposed within the catheter 300 with the expandable basket 410 in a collapsed configuration. FIG. 3 illustrates the expandable basket 410 disposed out of the catheter 300 with the expandable basket 410 disposed in an expanded configuration.

In the illustrated embodiment, the macerating element 400 comprises the expandable basket 410, a first torque cable 420, and a second torque cable 430. In the illustrated embodiment, the second torque cable 430 is coupled to the proximal end 414 of the expandable basket 410 at a distal end 432 of the second torque cable 430. Also, in the illustrated embodiment, the first torque cable 420 is disposed within the second torque cable 430 and within the expandable basket 410, and is coupled to a distal end of the expandable basket 410. The second torque cable 430 and the first torque cable 420 may be configured to move relative to each other in the axial direction.

The first torque cable 420 may include a lumen disposed within. The first torque cable 420 may include an opening 422 disposed at a distal end 424 of the first torque cable 420 that is in communication with the lumen. The guidewire 500 may be advanced through the handle 200 and through the lumen of the first torque cable 420. As discussed previously, the lumen in the first torque cable 420 may be used for aspiration and/or infusion, including for medication, saline, clots etc.

The macerating element 400 may further include a second lumen. The second lumen may be disposed between the first torque cable 420 and the second torque cable 430, in other words, the second lumen may comprise an annular space between the first torque cable 420 and the second torque cable 430. As discussed previously, the second lumen may be used for aspiration and/or infusion. In some embodiments, the second lumen may be in fluid communication with the third port 260.

In some embodiments, a third lumen may be disposed between the second torque cable 430 and the catheter 300. This lumen may also be used for aspiration and/or infusion. In some embodiments, the third lumen may be in fluid communication with the third port 260 in addition to, or instead of, communication between the third port 260 and the second lumen. In some embodiments, the third lumen may be in fluid communication with a fourth port (not shown). In such embodiments, the second lumen and the third lumen may be separately used for aspiration and/or infusion.

As shown in the figures, the expandable basket 410 may comprise a plurality of struts 412. In the illustrated embodiment, each strut 412 extends from a proximal end 414 of the expandable basket 410 to a distal end 416 of the expandable basket 410. The expandable basket 410 is coupled to the second torque cable 430 at the proximal end 414 of the expandable basket 410 and the distal end 432 of the second torque cable 430. The expandable basket 410 is also coupled to the first torque cable 420 at the distal end 416 of the expandable basket 410 and the distal end 424 of the first torque cable 420.

The expandable basket 410 may be collapsed and expanded in a number of different ways. For example, the struts 412 of the expandable basket 410 may be made of a memory material, such as Nitinol, so that the expandable basket 410 may achieve a predetermined shape when the expandable basket 410 is unsheathed. The catheter 300 may sheath the expandable basket 410 and apply the appropriate amount of pressure to the expandable basket 410 to keep the expandable basket 410 in the collapsed configuration when the expandable basket 410 is disposed within the catheter 300. The unsheathing may occur when the expandable basket 410 is either advanced out of the catheter 300 or when the catheter 300 is drawn back, enabling the expandable basket 410 to expand to its expanded predetermined configuration.

In another embodiment, axial movement of the first torque cable 420 relative to the second torque cable 430 may expand and collapse the expandable basket 410. As discussed previously, the proximal end 414 of the expandable basket 410 may be coupled to the distal end 432 of the second torque cable 430 and the proximal end 414 of the expandable basket 410 may be coupled to the distal end 424 of the first torque cable 420. In such embodiments, distal displacement of the second torque cable 430 relative to the first torque cable 420 may be configured to exert a longitudinal compressive force on the struts 412 and expand the expandable basket 410. Similarly, proximal displacement of the second torque cable 430 relative to the first torque cable 420 may be configured to collapse the expandable basket 410.

In another embodiment, a proximally oriented force applied to the first torque cable 420 may be configured to displace the first torque cable 420 proximally relative to the second torque cable 430 and expand the expandable basket 410. Similarly, a distally oriented force applied to the first torque cable 420 may be configured to displace the first torque cable 420 distally relative to the second torque cable 430 and collapse the expandable basket 410.

For some embodiments, in the collapsed configuration, the diameter of the expandable basket 410 may range from 1 mm to 5 mm. Further, for some such embodiments, in an expanded configuration, the diameter of the expandable basket 410 may range from 5 mm to 30 mm.

FIG. 4A illustrates an exemplary torque cable 600, the structure of which is described in more detail below. As in the illustrated embodiment, the torque cable 600 may have a tubular shaft shape. The following description of the torque cable 600 may apply to either the first torque cable 420 or the second torque cable 430. In other words, cables within the scope of the disclosure relating to the exemplary torque cable 600 may be utilized either (or both) the first torque cable 420 and/or the second torque cable 430 in the macerating device 100 described above. The torque cable 600 comprises a proximal end 602 and a distal end 604. In some embodiments, the proximal end 602 of the torque cable 600 may be coupled to a motor that rotates the torque cable 600. When utilized as an element of the macerating device, a distal end 604 of the torque cable 600 may be coupled to the expandable basket 410. As discussed above, the first torque cable 420 (which may comprise a torque cable of the design of torque cable 600) may be coupled to a distal end 416 of the expandable basket 410 and the second torque cable 430 (which may comprise a torque cable of the design of torque cable 600) may be coupled to a proximal end 414 of the expandable basket 410.

In some embodiments, cables such as torque cable 600, may comprise coils disposed around a central axis. A further detailed below, application of torque to a coil may tend to cause the coil to radially compress or radially expand, depending on the features of the coil (such as the direction of the coil) and the direction of the applied torque. As also detailed below, cables comprising multiple coils (including multiple coils within the same radial layer and those including multiple coils in different radial layers) may be configured to interact to reduce radial compression and/or expansion and to transfer torque.

Reference is made herein to the direction of coils. As used herein, the direction of a coil is defined as follows. When the coil is viewed from a distal end of the coil, and the wire of the coil followed in a clockwise direction, if the wire of the coil extends distally along the longitudinal axis of the coil, the coil is hereby defined as directed in the distal direction. Similarly, when the coil is viewed from the distal end of the coil, and the wire of the coil followed in a clockwise direction, if the wires of the coil extend proximally along the longitudinal axis of the coil, the coil is defined as directed in the proximal direction.

The torque cable 600 may comprise a plurality of radial layers. In the illustrated embodiment, the torque cable 600 comprises an inner layer 610 and an outer layer 620. Embodiments with additional layers, such as embodiments with four radial layers are within the scope of this disclosure. Further, it is noted that though the first torque cable 420 and second torque cable 430 may be disposed in a coaxial arrangement, the radial layers discussed in connection to torque cable 600 may be present in either or both the first torque cable 420 and second torque cable 430, and the references below to inner and outer radial layers should not be construed as referencing the coaxial arrangement of the first torque cable 420 and second torque cable 430 when assembled as part of the macerator device 100.

FIG. 4B is a breakaway view of the torque cable 600 that illustrates an inner layer 610 and an outer layer 620. The inner layer 610 and outer layer 620 may be configured to interact to maintain a constant diameter of the torque cable 600 when torque is applied to the torque cable 600 and, in turn, efficiently transfer torque along the torque cable 600. For example, and as further detailed below, the layers 610 and 620 of the torque cable 600 may be designed so that during application of torque to the torque cable 600 the outer layer 620 may tend to compress radially and the inner layer 610 may tend to expand radially. The interaction of these layers may thus counteract, such that the overall diameter of the torque cable 600 does not change, or is minimized, during application of torque to the torque cable 600. In use, such torque may be applied during a macerating procedure where the torque cable is rotating to macerate a clot, including resistance to the rotation applied by the clot or other obstruction interacting with the expandable basket 410. Again, forces tending to radially compress the outer layer 620 may counteract forces tending to radially expand the inner layer 610 (and forces that tend to radially expand the inner layer 610 may counteract the compression of the outer layer 620). This interaction may thus facilitate more efficiently the transfer of torque along the length of the torque cable 600.

Figure 5:
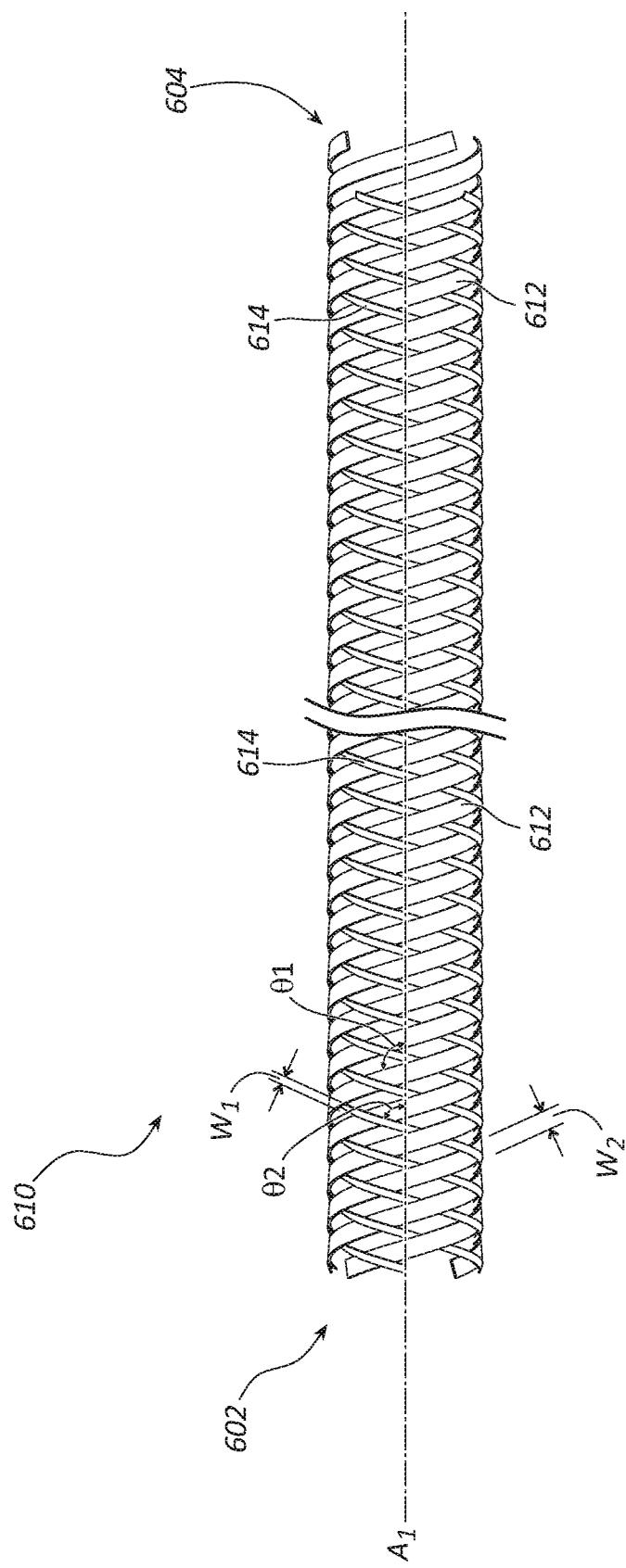
FIG. 5 is a side view of an inner layer of the torque cable of FIGS. 4A and 4B.

FIG. 5 illustrates the inner layer 610 comprises a plurality of wires (arranged in coils in the illustrated embodiment) that coil around a longitudinal axis A1 of the torque cable 600. The plurality of wires form a braiding pattern. As detailed below, the braiding pattern may be a full-load pattern, a half-load pattern, a diamond pattern, and the like.

The plurality of wires of the inner layer 610 may comprise a first set of wires 612 that are directed in a proximal direction and a second set of wires 614 that are directed in the distal direction. In other words, coils that comprise the inner layer 610 (or any radial layer) may be configured to be disposed in opposite directions. That is, when viewed from the distal end 604 and followed in a clockwise direction around the longitudinal axis A1, the first set of wires 612 extends along the longitudinal axis A1 in a proximal direction, thus as defined above, the first set of wires 612 extend in the proximal direction. Further, when viewed from the distal end 604 and followed in a clockwise direction around the longitudinal axis A1, the second set of wires 614 extends along the longitudinal axis A1 in a distal direction, thus as defined above, the second set of wires 614 extend in the distal direction. In some embodiments, the direction of the wires may be reversed, e.g., the first set of wires 612 may be directed in the distal direction and the second set of wires 614 may be directed in the proximal direction.

In addition to the direction, proximal, of the first set of wires 612 of the illustrated embodiment, the coils of the first set of wires 612 define a pitch, or the angle at which the coils are disposed with respect to the longitudinal axis A1 of the coil. In the illustrated embodiment, the first set of wires 612 are disposed at a first angle $\theta_1$ with respect to the longitudinal axis A1 of the torque cable 600. The first angle $\theta_1$ may be between 90 and 180 degrees. In some embodiments, the first angle $\theta_1$ may be between 95 and 150 degrees. In some embodiments, the first angle $\theta_1$ may be between 100 and 130 degrees.

Similarly, in addition to the direction, distal, of the second set of wires 614 of the illustrated embodiment, the coils of the second set of wires 614 define a pitch, or the angle at which the coils are disposed with respect to the longitudinal axis A1 of the coil. In the illustrated embodiment, the second set of wires 614 are disposed at a second angle $\theta_2$ with respect to the longitudinal axis A1 of the torque cable 600. The second angle $\theta_2$ may be between 0 and 90 degrees. In some embodiments the second angle $\theta_2$ may be between 30 and 85 degrees. In some embodiments, the second angle $\theta_2$ may be between 55 and 85 degrees.

In some embodiments, the first set of wires 612 and the second set of wires 614 may differ in size or may have the same dimensions. In the illustrated embodiment, the first set of wires 612 have a first width $W_1$ and the second set of wires 614 have a second width $W_2$. The first width $W_1$ may range between 0.00025 inches and 0.100 inches. In some embodiments the first width $W_1$ may range between 0.001 inches and 0.020 inches. In some embodiments, the first width $W_1$ may range between 0.0025 inches and 0.010 inches. The second width $W_2$ may range between 0.00025 inches and 0.100 inches. In some embodiments, the second width $W_2$ may range between 0.001 inches and 0.020 inches. In some embodiments, the second width $W_2$ may be between 0.0025 inches and 0.010 inches. In some embodiments, the width $W_1$ of the first set of wires 612 is at least twice the width $W_2$ of the second set of wires.

In some embodiments, the wires of the inner layer 610 may have a circular cross-section. In other embodiments, the wires of the inner layer 610 may be a flattened cross-section with round edges 615.

Figure 6:
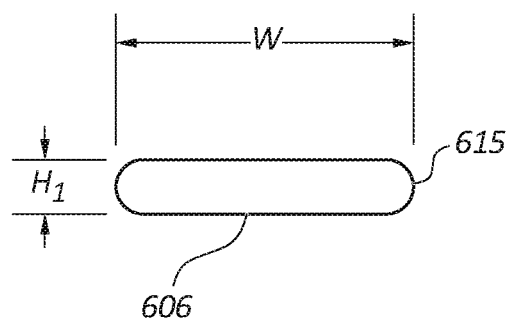
FIG. 6 is a cross-sectional view of a wire of the torque cable of FIGS. 4A and 4B.

FIG. 6 illustrates a flattened wire 606 with a height Hi that ranges between 0.00025 inches and 0.100 inches. In some embodiments, the height Hi may range between 0.00025 inches and 0.010 inches. In some embodiments, the height Hi may range between 0.00025 inches and 0.005 inches. The width W of the wire 606 may have the width dimensions of either $W_1$ or $W_2$.

In the illustrated embodiment, the inner layer 610 comprises four wires in each set. The first set of wires 612 comprises four wires that coil in a proximal direction. The second set of wires 614 comprises four wires that coil in a distal direction. The present disclosure includes embodiments with more or fewer than four wires in each set.

Figure 7A:
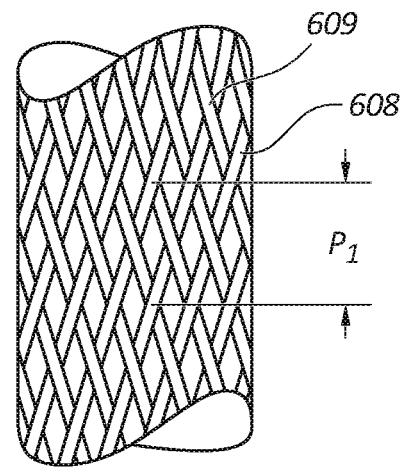
FIG. 7A shows a half-load braiding pattern of a torque cable according to one embodiment.
Figure 7B:
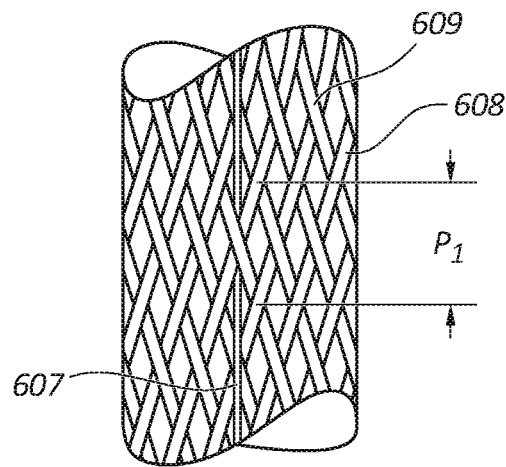
FIG. 7B shows a half-load braiding pattern of a torque cable with an additional axial strand, according to one embodiment.

As discussed above, the inner layer 610 forms a braiding pattern. The braiding pattern is formed by braiding the first set of wires 612 and the second set of wires 614, noting the first set of wires 612 and second set of wires 614 extend in opposite directions. In some embodiments, the braiding pattern is a half-load braiding pattern. Accordingly, the first set of wires 612 is braided in an over-under pattern with the second set of wires 614. In other words, a wire of the first set of wires 612 alternately goes over one wire of the second set of wires 614, under another wire of the second set of wires 614, and over another wire of the second set of wires 614, etc. until the wire reaches the proximal end 602 of the torque cable 600. The wires from the second set of wires 614 are braided in a similar pattern with the first set of wires 612 as described above. FIG. 7A illustrates a half-load pattern in which a single weft wire 608 alternately passes under then over a warp wire 609. In some embodiments, as shown in FIG. 7B, the inner layer 610 comprises a half-load braiding pattern in which a single weft wire 608 alternately passes under then over a warp wire 609 and further includes an axial strand 607. In some embodiments, the inner layer 610 may include one or more axial stands 607, and the axial stands 607 may be equally spaced apart along the circumference of the inner layer 610. The one or more axial strands 607 are configured to add additional tensile strength to the inner layer 610.

Figure 8A:
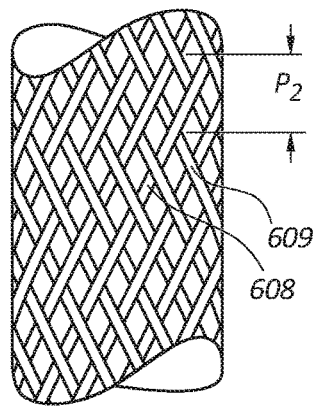
FIG. 8A shows a full-load braiding pattern of a torque cable according to one embodiment.
Figure 8B:
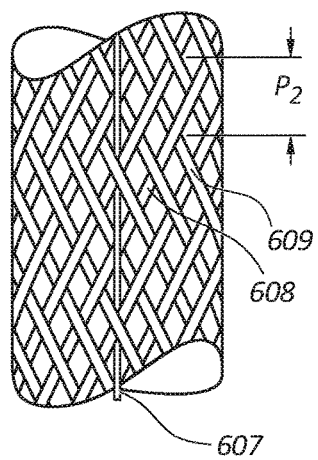
FIG. 8B shows a full-load braiding pattern of a torque cable with an axial strand, according to one embodiment.

In some embodiments, the braiding pattern is a full-load braiding pattern. Accordingly, the first set of wires 612 is braided in a two-over, two-under pattern with the second set of wires 614 that rotate in an opposite direction of the first set of wires 612. In other words, a wire of the first set of wires 612 alternately goes over two wires of the second set of wires 614, under another two wires of the second set of wires 614, over another two wires of the second set of wires 614, etc. until the wire reaches the proximal end 602 of the torque cable 600. The wires from the second set of wires 614 are braided in a similar pattern with the first set of wires 612 as described above. FIG. 8A illustrates a full-load pattern in which a single weft wire 608 passes under two warp wires 609 and then over two warp wires 609. In some embodiments, as shown in FIG. 8B, the inner layer 610 comprises a full-load pattern in which a single weft wire 608 passes under two warp wires 609 and then over two warp wires 609 and further includes an axial strand 607. In some embodiments, the inner layer 610 may include one or more axial stands 607, and the axial stands 607 may be equally spaced apart along the circumference of the inner layer 610. The one or more axial strands 607 are configured to add additional tensile strength to the inner layer 610.

Figure 9A:
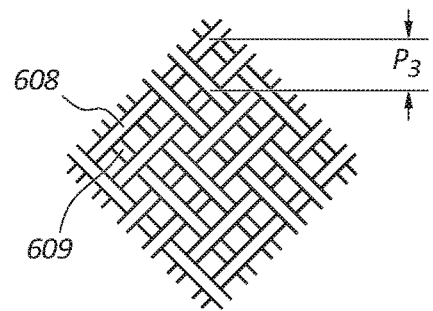
FIG. 9A shows a diamond braiding pattern of a torque cable according to one embodiment.
Figure 9B:
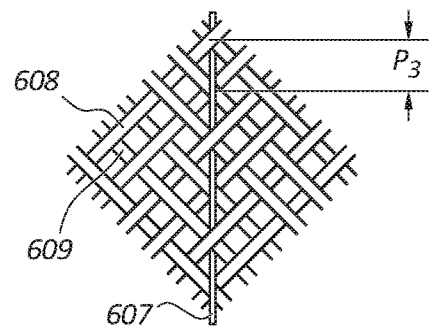
FIG. 9B shows a diamond braiding pattern of a torque cable with an axial strand, according to one embodiment.

In some embodiments, the braiding pattern is a diamond braiding pattern. Accordingly, the two wires, side by side, of the first set of wires 612 is braided in a two-over, two-under pattern with the second set of wires 614. In other words, two wires, side by side, of the first set of wires 612 alternately go over two wires of the second set of wires 614, under another two wires of the second set of wires 614, over another two wires of the second set of wires 614, etc. until the two wires reach the proximal end 602 of the torque cable 600. The wires from the second set of wires 614 are braided in a similar pattern with the first set of wires 612 as described above. FIG. 9A illustrates a diamond pattern in which two weft wires 608 side by side alternately pass under two warp wires 609 and then pass over two warp wires 609. In some embodiments, as shown in FIG. 9B, the inner layer 610 comprises a diamond pattern in which two weft wires 608 side by side alternately pass under two warp wires 609 and then pass over two warp wires 609 and further includes an axial strand 607. In some embodiments, the inner layer 610 may include one or more axial stands 607, and the axial stands 607 may be equally spaced apart along the circumference of the inner layer 610. The one or more axial strands 607 are configured to add additional tensile strength to the inner layer 610.

The inner layer 610 may have a picks per inch (PPI) that ranges between 0 and 400. In some embodiments, the PPI may range between 30 to 200. In some embodiments, the PPI may range between 50 and 150. PPI defined by the number of weft wires 608 per inch. FIGS. 7, 8, and 9 each illustrates a single pick: P1, P2, and P3.

Figure 10:
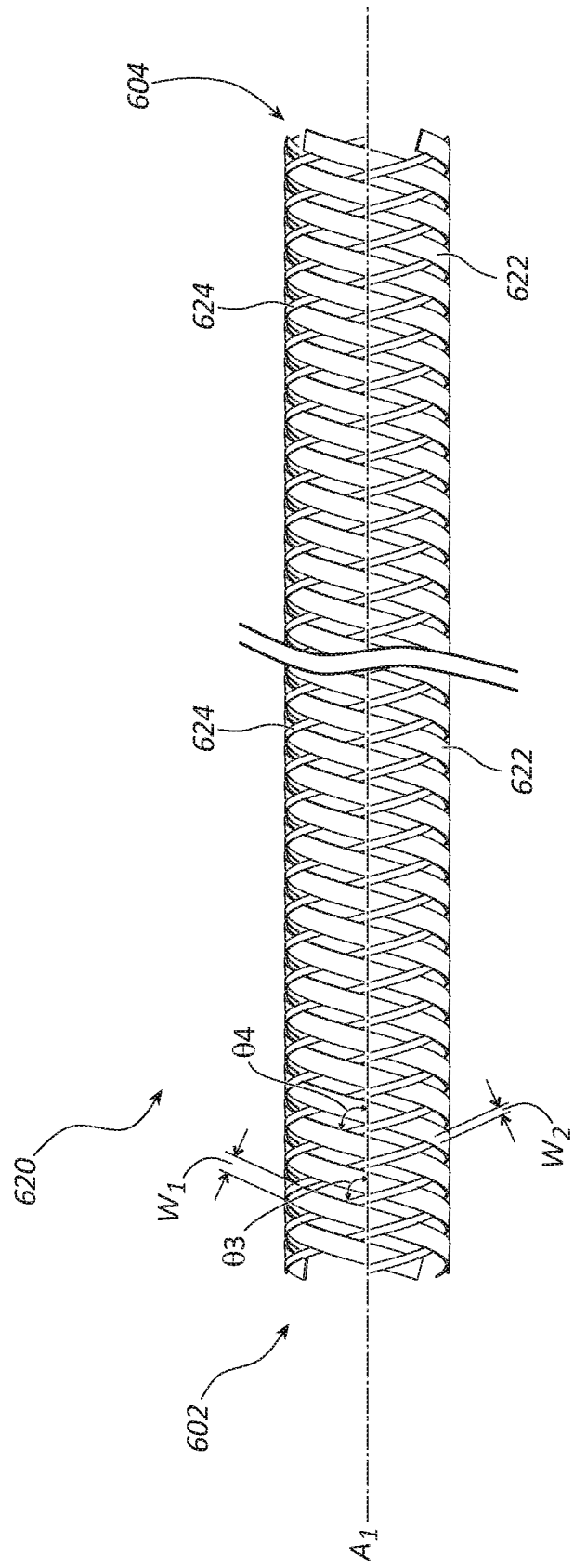
FIG. 10 is a side view of an outer layer of the torque cable of FIGS. 4A and 4B.

FIG. 10 illustrates the outer layer 620 comprises a plurality of wires (arranged in coils in the illustrated embodiment) that coil around the longitudinal axis A1 of the torque cable 600. The plurality of wires form a braiding pattern. As detailed below, the braiding pattern may be a full-load pattern, a half-load pattern, a diamond pattern, and the like.

The plurality of wires of the outer layer 620 may comprise a first set of wires 622 that are directed in a distal direction and a second set of wires 624 that are directed in a proximal direction. In other words, coils that comprise the outer layer 620 (or any radial layer) may be configured to be disposed in opposite directions. That is, when viewed from the distal end 604 and followed in a clockwise direction around the longitudinal axis A1, the first set of wires 622 extends along the longitudinal axis A1 in a proximal direction, thus as defined above, the first set of wires 622 extend in the proximal direction. Further, when viewed from the distal end 604 and followed in a clockwise direction around the longitudinal axis A1, the second set of wires 624 extends along the longitudinal axis A1 in a distal direction, thus as defined above, the second set of wires 624 extend in the distal direction. In some embodiments, the direction of the wires may be reversed, e.g., the first set of wires 622 may be directed in the proximal direction and the second set of wires 624 may be directed in the distal direction.

In addition to the direction, distal, of the first set of wires 622 of the illustrated embodiment, the coils of the first set of wires 622 define a pitch, or the angle at which the coils are disposed with respect to the longitudinal axis A1 of the coil. In the illustrated embodiment, the at a fourth angle $\theta_4$ off of the longitudinal axis A1 of the torque cable 600. The fourth angle $\theta_4$ may be between 0 and 90 degrees. In some embodiments, the fourth angle $\theta_4$ may be between 30 and 85 degrees. In some embodiments, the fourth angle $\theta_4$ may be between 55 and 85 degrees. In some embodiments, the fourth angle $\theta_4$ of the outer layer 620 is the same as the second angle $\theta_2$ of the inner layer 610.

Similarly, in addition to the direction, proximal, of the second set of wires 624 of the illustrated embodiment, the coils of the second set of wires 624 define a pitch, or, the angle at which the coils are disposed with respect to the longitudinal axis A1 of the coil. In the illustrated embodiment, the second set of wires 624 are disposed at a third angle $\theta_3$ with respect to the longitudinal axis A1 of the torque cable 600. The third angle 83 may between 90 and 180 degrees. In some embodiments, the third angle $\theta_3$ may be between 95 and 150 degrees. In some embodiments, the third angle $\theta_3$ may be between 100 and 130 degrees. In some embodiments, the third angle $\theta_3$ of the outer layer 620 is the same as the first angle $\theta_1$ of the inner layer 610.

In some embodiments, the first set of wires 622 may all have similar dimensions and the second set of wires 624 may all have similar dimensions. In some embodiments, the first set of wires 622 and the second set of wires 624 may differ in size or may have the same dimensions. In the illustrated embodiment, the first set of wires 622 have a first width $W_1$ and the second set of wires 624 have a second width $W_2$. The first width $W_1$ may range between 0.00025 inches and 0.100 inches. In some embodiments, the first width $W_1$ may range between 0.001 inches and 0.020 inches. In some embodiments, the first width $W_1$ may range between 0.0025 inches and 0.010 inches. The second width $W_2$ may range between 0.00025 inches and 0.100 inches. In some embodiments, the second width $W_2$ may range between 0.001 inches and 0.020 inches. In some embodiments, the second width $W_2$ may range between 0.0025 inches and 0.010 inches. In some embodiments, the width $W_2$ of the second set of wires 624 is at least twice the width $W_1$ of the first set of wires 622.

In some embodiments, the wires of the outer layer 620 may have a circular cross-section. In other embodiments, the wires of the outer layer 620 may be a flattened cross-section with round edges 615, similar to the flattened wire 606 of FIG. 6.

In the illustrated embodiment, the outer layer 620 comprises four wires in each set. The first set of wires 622 comprises four wires that coil in a distal direction. The second set of wires 624 comprises four wires that coil proximal direction. The present disclosure includes embodiments with more or fewer than four wires in each set.

As discussed above, the outer layer 620 forms a braiding pattern. The braiding pattern is formed by braiding the first set of wires 622 and the second set of wires 624, noting the first set of wires 622 and the second set of wires 624 extend in opposite directions. In some embodiments, the braiding pattern is a half-load braiding pattern. Accordingly, the first set of wires 622 is braided in an over-under pattern with the second set of wires. In other words, a wire of the first set of wires 622 alternately goes over one wire of the second set of wires 624, under another wire of the second set of wires 624, and over another wire of the second set of wires 624, etc. until the wire reaches the distal end 604 of the torque cable 600. The wires from the second set of wires 624 are braided in a similar pattern with the first set of wires 622 as described above. FIG. 7A illustrates a half-load pattern in which a single weft wire 608 alternately passes under then over the warp wire 609. In some embodiments, as shown in FIG. 7B, the outer layer 620 comprises a half-load braiding pattern in which a single weft wire 608 alternately passes under then over a warp wire 609 and further includes an axial strand 607. In some embodiments, the outer layer 620 may include one or more axial stands 607, and the axial stands 607 may be equally spaced apart along the circumference of the outer layer 620. The one or more axial strands 607 are configured to add additional tensile strength to the outer layer 620.

In some embodiments, the braiding pattern is a full-load braiding pattern. Accordingly, the first set of wires 622 is braided in a two-over, two-under pattern with the second set of wires 624 that rotate in an opposite direction of the first set of wires. In other words, a wire of the first set of wires 622 alternately goes over two wires of the second set of wires 624, under another two wires of the second set of wires 624, over another two wires of the second set of wires 624, etc. until the wire reaches the distal end 604 of the torque cable 600. The wires from the second set of wires 624 are braided in a similar pattern with the first set of wires 622 as described above. FIG. 8A illustrates a full-load pattern in which a single weft wire 608 passes under two warp wires 609 and then over two warp wires 609. In some embodiments, as shown in FIG. 8B, the outer layer 620 comprises a full-load pattern in which a single weft wire 608 passes under two warp wires 609 and then over two warp wires 609 and further includes an axial strand 607. In some embodiments, the outer layer 620 may include one or more axial stands 607, and the axial stands 607 may be equally spaced apart along the circumference of the outer layer 620. The one or more axial strands 607 are configured to add additional tensile strength to the inner layer 610.

In some embodiments, the braiding pattern is a diamond braiding pattern. Accordingly, the two wires, side by side, of the first set of wires 622 is braided in a two-over, two-under pattern with the second set of wires 624. In other words, two wires, side by side, of the first set of wires 622 alternately go over two wires of the second set of wires 624, under another two wires of the second set of wires 624, over another two wires of the second set of wires 624, etc. until the two wires reach the distal end 604 of the torque cable 600. The wires from the second set of wires 624 are braided in a similar pattern with the first set of wires as described above. FIG. 9A illustrates a diamond pattern in which two weft wires 608 side by side alternately pass under two warp wires 609 and then pass over two warp wires 609. In some embodiments, as shown in FIG. 9B, the outer layer 620 comprises a diamond pattern in which two weft wires 608 side by side alternately pass under two warp wires 609 and then pass over two warp wires 609 and further includes an axial strand 607. In some embodiments, the outer layer 620 may include one or more axial stands 607, and the axial stands 607 may be equally spaced apart along the circumference of the outer layer 620. The one or more axial strands 607 are configured to add additional tensile strength to the outer layer 620.

The outer layer 620 may have a PPI that ranges between 0 and 400. In some embodiments, the PPI may range between 30 to 200. In some embodiments, the PPI may range between 50 and 150. PPI is defined by the number of weft wires 608 per inch. FIGS. 7, 8, and 9 each illustrate a single pick: P1, P2, and P3. In some embodiments, the PPI of the inner layer 610 and the PPI of the outer layer 620 are the same. In some embodiments, the PPI of the inner layer 610 is greater than the PPI of the outer layer 620. In some embodiments, the PPI of the inner layer 610 is less than the PPI of the outer layer 620.

Figure 11:
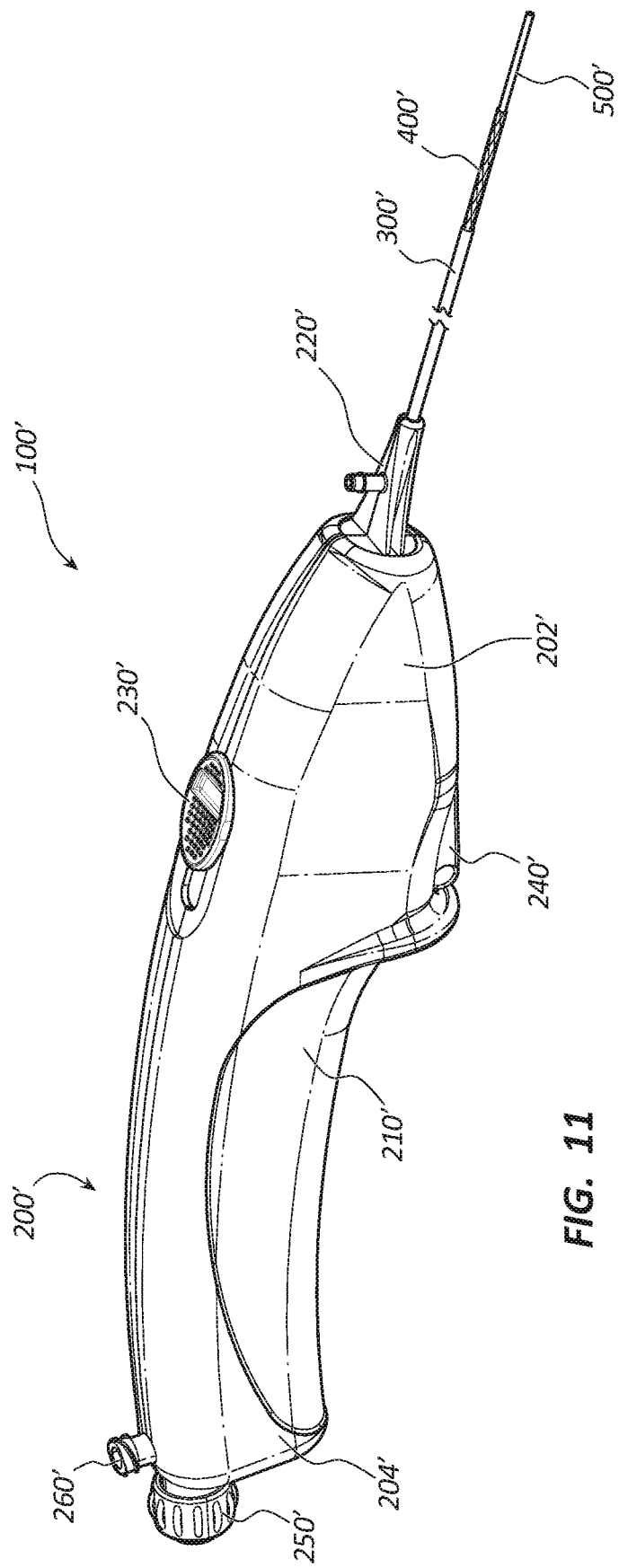
FIG. 11 shows a perspective view of a thrombosis macerating device comprising a handle and a catheter according to one embodiment.

FIG. 11 depicts an embodiment of a macerating device 100' that resembles the macerating device 100 described above in certain respects. Accordingly, like features are designated with like reference numerals with an apostrophe added. For example, the embodiment depicted in FIG. 11 includes a handle 200' that may, in some respects, resemble the handle 200 of FIG. 1. The handle 200' in the illustrated embodiment of FIG. 11 is designed to include an ergonomical handle to minimize user discomfort when gripping the handle 200'. Relevant disclosure set forth above regarding similarly identified features, such as the distal portion 202', the proximal portion 204', the housing 210', the coupler 220', the trigger 230', the slider 240', the second port 250', the third port 260', the catheter 300', the macerating element 400', and the guidewire 500', are not repeated hereafter.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A torque cable comprising:
an inner layer comprising a plurality of coils that form a braiding pattern, wherein a first set of coils of the inner layer is directed in a proximal direction and a second set of coils of the inner layer is directed in a distal direction; and
an outer layer comprising a plurality of coils that form a braiding pattern, wherein a first set of coils of the outer layer is directed in a proximal direction and a second set of coils of the outer layer is directed in a distal direction,
wherein the inner layer is in direct contact with the outer layer;
wherein the inner layer is configured to directly interact with the outer layer during rotation of the torque cable, wherein the inner layer and the outer layer are configured to move relative to each other in an axial direction, wherein a width of the first set of coils of the inner layer is at least twice of a width of the second set of coils of the inner layer, wherein a width of the second set of coils of the outer layer is at least twice of a width of the first set of coils of the inner layer, and wherein each of the widths of the first and second coils of the inner layer and the widths of the first and second coils of the outer layer are constant along a length of the torque cable.

2. The torque cable of claim 1, wherein the braiding pattern of the inner layer comprises a half-load pattern.

3. The torque cable of claim 1, wherein the braiding pattern of the inner layer comprises a full-load pattern.

4. The torque cable of claim 1, wherein the braiding pattern of the inner layer comprises a diamond pattern.

5. The torque cable of claim 1, wherein the first set of coils of the inner layer rotate in a first direction and the second set of coils of the inner layer rotate in a second direction, wherein the first direction is different from the second direction.

6. The torque cable of claim 5, wherein the second direction is opposite the first direction.

7. The torque cable of claim 6, wherein the first set of coils of the inner layer rotate in the first direction at an angle between 90 and 180.

8. The torque cable of claim 1, wherein a picks per inch of the inner layer range from 0 to 400.

9. The torque cable of claim 1, wherein the plurality of coils of the inner and outer layer comprise a flattened configuration with round edges.

10. The torque cable of claim 1, wherein the first set of coils of the inner layer and the second set of coils of the inner layer comprise four coils.

11. The torque cable of claim 1, wherein the inner layer further comprises at least one axial strand that is braided with the plurality of coils of the inner layer, and wherein the at least one axial strand extends from a proximal end of the torque cable to a distal end of the torque cable.

12. The torque cable of claims 11, wherein the outer layer further comprises at least one axial strand that is braided with the plurality of coils of the outer layer, and wherein the at least one axial strand extends from the proximal end of the torque cable to the distal end of the torque cable.

13. A torque cable comprising:
an inner layer comprising a plurality of wires that form a braiding pattern, wherein rotation of the torque cable expands the inner layer; and
an outer layer comprising a plurality of wires that form a braiding pattern, wherein rotation of the torque cable compresses the outer layer,
wherein the inner layer is in direct contact with the outer layer;
wherein during rotation of the torque cable the inner layer radially expands and the outer layer radially compresses such that the inner layer and the outer layer directly interact with each other to maintain a diameter of the torque cable during rotation, and
wherein the inner layer and the outer layer are configured to move relative to each other in an axial direction.

14. The torque cable of claim 13, wherein a first set of wires of the inner layer rotate in a counterclockwise direction along a longitudinal length of the torque cable toward a proximal end of the torque cable, and a second set of wires of the inner layer rotate in a clockwise direction along the longitudinal length of the torque cable toward a distal end of the torque cable.

15. The torque cable of claim 13, wherein a first set of wires of the outer layer rotate in a clockwise direction along a longitudinal length of the torque cable toward a distal end of the torque cable, and a second set of wires of the outer layer rotate in a counterclockwise direction along the longitudinal length of the torque cable toward a proximal end of the torque cable.

16. The torque cable of claim 13, wherein a picks per inch of the inner layer and the outer layer is the same.

17. The torque cable of claim 13, wherein the inner layer further comprises at least one axial strand that is braided with the plurality of wires of the inner layer, and wherein the axial strand extends from a proximal end of the torque cable to the distal end of the torque cable.

* * * * *